US012718921B2

(12) United States Patent
Weiss et al.

(10) Patent No.: US 12,718,921 B2
(45) Date of Patent: Aug. 25, 2026

(54) ENHANCEMENT AND STABILIZATION GLP AND GPI DRUG EFFECTS ON THE LIMBIC SYSTEM BY PROVIDING DIGITAL COGNITIVE BEHAVIORAL THERAPY

(71) Applicant: GAIA AG, Hamburg (DE)

(72) Inventors: Mario Weiss, Hamburg (DE); Tristan Zindler, Hamburg (DE); Bernhard Wellhöfer, Hamburg (DE)

(73) Assignee: GAIA AG, Hamburg (DE)

( * ) Notice: Subject to any disclaimer, the term of this patent is extended or adjusted under 35 U.S.C. 154(b) by 0 days.

(21) Appl. No.: 18/966,586

(22) Filed: Dec. 3, 2024

(65) Prior Publication Data

US 2026/0155225 A1 Jun. 4, 2026

(51) Int. Cl.
*G16H 20/10* (2018.01)
*G16H 20/70* (2018.01)
*G16H 80/00* (2018.01)

(52) U.S. Cl.
CPC ............. *G16H 20/10* (2018.01); *G16H 20/70* (2018.01); *G16H 80/00* (2018.01)

(58) Field of Classification Search
CPC ......... G16H 20/10; G16H 20/70; G16H 80/00
See application file for complete search history.

(56) References Cited

U.S. PATENT DOCUMENTS

| | | | | |
|---|---|---|---|---|
| 12,205,694 | B2 * | 1/2025 | Kapaldo | G06N 5/04 |
| 2020/0350073 | A1 * | 11/2020 | Goldsmith | G16H 40/67 |
| 2022/0115133 | A1 | 4/2022 | Mason et al. | |
| 2023/0317230 | A1 * | 10/2023 | Sartain | A61B 5/7264 |

FOREIGN PATENT DOCUMENTS

| | | | | |
|---|---|---|---|---|
| CN | 108780663 | B | 12/2022 | |
| CN | 109243605 | B | 12/2022 | |
| WO | WO-2022200434 | A1 * | 9/2022 | A61M 16/026 |

OTHER PUBLICATIONS

Clements, Mark A et al. "Using Digital Health Technology to Prevent and Treat Diabetes." Diabetes Technology & Therapeutics. vol. 26, Supplement 1, 2024 (Year: 2024).*
Chul Ko, Byoung; "A Brief Review of Facial Emotion Recognition Based on Visual Information"; MDPI, Sensors; Jan. 30, 2018; 20 Pages.
Mehta, Dhwani, et al; "Facial Emotion Recognition: A Survey and Real-World User Experiences in Mixed Reality"; MDPI, Sensors—Wearable Smart Devices, vol. 18, Issue 2; Basel, Switzerland; Feb. 1, 2018; 24 Pages.
Abd-Alrazaq, Alaa A., et al; "An overview of the features of chatbots in mental health: A scoping review"; International Journal of Medical Informatics; vol. 132; Science Direct, Elsevier; Dec. 2019; 8 Pages.

(Continued)

*Primary Examiner* — Linh Giang Le
(74) *Attorney, Agent, or Firm* — Whitmyer IP Group LLC

(57) ABSTRACT

Psychotherapy techniques can lead to significant changes in the limbic system of a patient, thereby enhancing emotional regulation, reducing impacts of stress, facilitating healthier memory processing, and supporting behavioral changes. These transformations are essential to the effectiveness of therapy in treating emotional and psychological disorders in a given patient.

11 Claims, 8 Drawing Sheets

(56) References Cited

OTHER PUBLICATIONS

Brown, Tom B., et al.; "Language Models are Few-Shot Learners"; ArXiv, Computer Science—Computation and Language, Cornell University; Jul. 22, 2020; 75 Pages.
Dalvi, Chirag, et al.; "A Survey of AI-Based Facial Emotion Recognition: Features, ML & DL Techniques, Age-Wise Datasets and Future Directions"; IEEE, vol. 9; Nov. 30, 2021; 35 Pages.
Tanana, Michael J., et al.; "How do you feel? Using Natural language processing to automatically rate emotion in psychotherapy"; Behavior Research Methods; Springer; Mar. 22, 2021; 21 Pages.
Piccoli, Benedetto; "Control of multi-agent systems: results, open problems, and applications"; ArXiv, Mathematics—Optimization and Control, Cornelle University; Feb. 2023; 41 Pages.
Tauscher, Justin S., et al; "Automated Detection of Cognitive Distortions in Text Exchanges Between Clinicians and People With Serious Mental Illness"; American Psychiatric Association, Psychiatric Services, vol. 74, No. 4; Apr. 1, 2023; 4 Pages.
Casu, Mirko, et al; "AI Chatbots for Mental Health: A Scoping Review of Effectiveness, Feasibility, and Applications"; MDPI, Applied Sciences, vol. 14, Issue 13, Innovative Digital Health Technologies and Their Applications; Basel, Switzerland; Jul. 5, 2024; 23 Pages.
Du, Zhuoyun, et al.; "Multi-Agent Software Development through Cross-Team Collaboration"; ArXiv, Computer Science—Computation and Language, Cornell University; Jun. 13, 2024; 17 Pages.
Guo, Taicheng, et al.; "Large Language Model based Multi-Agents: A Survey of Progress and Challenges"; ArXiv, Computer Science—Computation and Language, Cornell University; Apr. 19, 2024; 15 Pages.
Held, Philip, et al.; "A Novel Cognitive Behavioral TherapyBased Generative AI Tool (Socrates 2.0) to Facilitate Socratic Dialogue: Protocol for a Mixed Methods Feasibility Study"; JMIR Research Protocols, vol. 13; Oct. 13, 2024; 15 Pages.
Jiang, Meng, et al.; "A Generic Review of Integrating Artificial Intelligence in Cognitive Behavioral Therapy"; Aug. 5, 2024; 43 Pages.
Jiang, Meng; "AI-Enhanced Cognitive Behavioral Therapy: Deep Learning and Large Language Models for Extracting Cognitive Pathways from Social Media Texts"; ArXiv, Computer Science—Computation and Language, Cornell University; Apr. 17, 2024; 29 Pages.
Kampman, Onno P., et al.; "A Multi-Agent Dual Dialogue System to Support Mental Health Care Providers"; ArXiv, Computer Science—Human-Computer Interaction, Cornell University; Nov. 28, 2024; 16 Pages.
Li, Ao, et al.; "Agent-Oriented Planning in Multi-Agent Systems"; ArXiv, Computer Science—Artificial Intelligence, Cornell University; Oct. 3, 2024; 20 Pages.
Naveed, Humza, et al.; "A Comprehensive Overview of Large Language Models"; ArXiv, Computer Science—Computation and Language Cornell University; Feb. 28, 2024; 90 Pages.
Wang, Ruiyi, et al.; "Patient-?: Using Large Language Models to Simulate Patients for Training Mental Health Professionals"; ArXiv, Computer Science—Computation and Language, Cornell University; Oct. 3, 2024; 26 Pages.
Gual-Montolio, Patricia, et al.; "Using Artificial Intelligence to Enhance Ongoing Psychological Interventions for Emotional Problems in Real- or Close to Real-Time: A Systematic Review"; MDPI, International Journal of Environmental Research and Public Health, vol. 19, Issue 3; Jun. 24, 2022; 21 Pages.

* cited by examiner

Character

Therapeutic Clinical Narrative

Last Messages

Last Inner Voice

Constraints and Instructions

Current Time

700

ENHANCEMENT AND STABILIZATION GLP AND GPI DRUG EFFECTS ON THE LIMBIC SYSTEM BY PROVIDING DIGITAL COGNITIVE BEHAVIORAL THERAPY

TECHNICAL FIELD

GLP-1 and GIP drugs are commonly prescribed to patients for the purpose of managing the caloric intake of a patient. Cognitive behavioral therapy techniques can increase the effectiveness and stability of patients prescribed these drugs and sustain the positive effects of those drugs after patients have discontinued the prescription.

BACKGROUND

Glucagon-like peptide-1 ("GLP-1") and glucose-dependent insulinotropic polypeptide ("GIP") function as hormones which directly influence the appetite centers in the brain, particularly the hypothalamus. GLP-1 and GIP hormones increase satiety (e.g., the feeling of being full) and decrease hunger, which results in a lowering of the overall caloric intake for the patient.

Semaglutide works by mimicking the GLP-1 hormone, which targets areas in the brain which regulate appetite and food intake. GLP-1 (and its synthetic imitator) slows the gastric emptying process (e.g., the consumption or conversion of the contents of the stomach into various subcomponents utilized by the body) and increases feelings of fullness or satiety in the body, resulting in lowered caloric intake for the patient.

Tirzepatide is a dual GLP-1 and GIP receptor agonist, which enhances the body's natural production of insulin (when blood sugar levels are high) and suppresses glucagon release (when blood sugar levels are low), thus reducing food intake in the patient through appetite regulation.

Patients who are prescribed GLP-1 or GIP drugs or hormones may substantially benefit from additional cognitive-behavioral therapy ("CBT") and other psychotherapeutic interventions. By targeting the same neuronal functions through a different mechanism(s) of action(s) than the chemical compounds prescribed to the patient, CBT and other psychotherapeutic interventions may enhance neuroplastic effects, memory processing, and stress-related functions in the brain. This synergy is expected to amplify the efficacy of the base prescribed drugs. Additionally, these interventions are likely to further modify eating behaviors, leading to improved clinical outcomes above and beyond those outcomes achieved by the base prescribed drugs. Further, CBT and other psychotherapeutic interventions may create sustained benefits in patients even after the base prescribed drugs are discontinued.

CBT and other psychotherapeutic interventions may be delivered through generative artificial intelligence systems ("GenAI") which interact or communicate with a patient. Presently, GenAI are prevalent. Such systems use statistical guessing to produce a most likely correct response to a prompt. They lack rigor in the algorithms that generate their responses, they are prone to mistaken guesses called "hallucinations", and there is not a high likelihood that a particular response will be "correct" in a useful sense of that term. Accordingly, GenAI is not appropriate for results-sensitive tasks.

An example of a results-sensitive task is Cognitive Behavioral Therapy (CBT), sometimes referred to as "talk therapy". In the CBT treatment modality, a patient or client converses with a trained professional to enhance the patient's functioning with any of a range of psychological disorders including depression, PTSD, etc. These same techniques may be applied to patients prescribed GLP-1 and GIP drugs for on (diabetes) or off-label (weight loss, though this is increasingly seeing direct approval by various regulatory bodies and thus is on-label) use.

Treatment sessions are traditionally held in person in a comfortable setting between therapist and patient in order to promote communication and engagement. The treatment seeks to help patients become more self-aware and recognize factors that influence their emotional well-being, and also to encourage supportive behaviors and activities so patients can reach their own emotional balance.

It is generally known that a series of regular CBT sessions is necessary to reinforce treatment initiatives until patients themselves become aware of improvements in their emotional state.

Ubiquitous Internet connectivity and the rise of mobile computing devices have made it possible for CBT to be consumed by patients without actually visiting a therapists' office. The patient's own environment and schedule can be more easily accommodated to not only leverage the patient's own comfort, but also to expand delivery of CBT services.

Computerized therapy systems are known, including systems for providing CBT, but these systems are only "intelligent" in the sense that they have the ability to answer a limited number of questions or provide a limited amount of information. Additionally, such systems have been only text-based. They either cannot accept inputs other than text, or they only provide replies in text, or both. So, the efficacy of existing computerized CBT systems is limited at least because the full range of a therapists' observations and experience cannot be used for treatment.

Further, current generation computerized therapy systems, including systems which may be operated as "chat bots," have trouble with logic and reasoning because they are fundamentally statistical guessing machines that produce the most "likely" response to a prompt. For example, existing systems may have trouble counting how many "r" letters are in the word "strawberry". The reasons for these troubles are fairly simple and also are fundamental to how these systems work (i.e., existing systems may represent "strawberry" as two or three tokens and count how many tokens have an "r"). When handling signals of intense emotional valence rather than spelling words, the potential for over-simplification by an unsupervised computerized therapy system could be counter-productive or even dangerous.

It would be desirable to provide a computerized CBT system that could generate responses with a relatively high likelihood of being "correct" as in usable for a results-sensitive purpose. Examples of results-sensitive purposes include dialogs that provide an end-user with therapeutic or advisory results; e.g., talk therapy, legal counseling, business advisement.

SUMMARY

According to aspects of the present disclosure, a psychotherapy system is provided which is designed to affect the brain, and particularly the limbic system crucial for emotional regulation, and thus improves and stabilizes the effects of GLP-1 and GIP drugs taken by a patient.

According to aspects of the present disclosure, a computerized CBT therapy system (herein also referred to as the "system") is provided that includes a mobile computing device; a messaging app running on the mobile computing device; a computer with access to the messaging app; a communication channel established between the mobile computing device and the computer; a message received by the computer from the mobile computing device over the communication channel; software executing in the computer for extracting at least one of audio, video and text data from the message, and for producing a summary; a database accessible by the computer for storing a history of the messages and summaries; software executing in the computer with access to the database (and, optionally, environmental factors) for generating an assessment of the message or of a conversation including the message; a database of curated replies, which may be processed to generate a numerical representation of each reply (optionally, the numerical representations may be stored with the replies); software executing in the computer for numerically representing the assessment (and/or the message) and for matching 127 the assessment (and/or the message) to one or more replies within the database, based on distances between the numerical representations; software executing in the computer for generating a reply to the message using at least one of the message, the summary, the assessment, and/or any matching curated content; and software executing in the computer for skeptically analyzing the reply and either returning it to the reply generating software for revision or forwarding it to the communication channel for transmission to the mobile computing device; wherein, once the reply is forwarded to the communication channel it is added to the database of messages to update a conversation including the message and the reply.

According to other aspects of the present disclosure, a computerized CBT therapy system is provided that includes a summarizer that is configured to receive one or more messages from a patient in at least one of audio, video, and text modalities, wherein the summarizer is further configured to produce and update a case summary based at least on the one or more messages; an inner voice that is configured to produce and update an assessment of the situation based at least on the case summary and a set of professional knowledge; and a composer that is configured to produce a reply to the patient based at least on the case summary and the assessment.

According to another aspect of the present disclosure, the computerized CBT therapy system may include a supervisor that is configured to provide feedback to the composer regarding the reply, wherein the composer is further configured to update the reply in response to the feedback. For example, the supervisor may be configured to provide the feedback based at least on the set of professional knowledge.

According to another aspect of the present disclosure, the computerized CBT therapy system may include a curated content injection system that is configured to receive the assessment and to provide curated content to the composer based at least on the assessment.

According to another aspect of the present disclosure, the summarizer may be further configured to produce and update the case summary based also on environmental factors.

According to another aspect of the present disclosure, the inner voice may be further configured to provide at least one motivational question to the composer based at least on the case summary, the set of professional knowledge, and the assessment.

According to another aspect of the present disclosure, the summarizer may be further configured to provide at least one gap-filling question to the composer based at least on the case summary.

According to another aspect of the present disclosure, the summarizer also may be configured to provide the at least one gap-filling question based also on the assessment.

Thus, aspects of the present disclosure can provide a computerized CBT therapy system that is available 24/7 to provide conversation patients with continuous contact. The system can be realized through a mobile text interface, for example, by texting a given number. Given the capabilities of speech-to-text and text-to-speech, as well as the ability for speaking video generation from 2-D still images and text, voice and video interfaces also are contemplated.

Such a system can provide patients timely and consistent support, regardless of time or location. By using advanced agent-based systems to deliver personalized responses, the system can focus on the individualized needs of patients, enhancing the accessibility and effectiveness of support.

Embodiments of a computerized CBT therapy system according to the present disclosure are not limited to a specific mode of communication. Such a system can support various communication platforms, such as a proprietary web app, WhatsApp, SMS (Simple Message Service), RCS (Rich Communication Services), iMessages, Signal, FaceTime or other text, voice, and/or video modalities. Thus, a computerized CBT therapy system according to aspects of the present disclosure may allow patients to choose their preferred communication method. Speech-to-text, text-to-speech, and text-to-video technologies enable consistent and seamless interaction across different platforms and enhance accessibility by catering to diverse user preferences and needs. The disclosed system delivers a cohesive user experience regardless of the communication channel used.

A multi-agent approach is a key aspect of the present disclosure. In the computerized CBT therapy system interaction, each reply is computed not in a single step but through a complex interplay of multiple agents. These agents distribute intermediate "cognitive" steps across multiple specialized requests to generate a supportive reply. Each agent is specialized in handling specific aspects of the reply-generation task, contributing to a more accurate and efficient overall response. The system can adapt to different support scenarios by reconfiguring the agents and their interactions. By distributing tasks among multiple agents, the system enhances resilience and fault tolerance, reducing the impact of any single point of failure. Specialized agents improve the likelihood that each aspect of the support algorithm is addressed with the highest level of expertise, improving the overall accuracy and effectiveness.

Key agents include a summarizer, an inner voice, a curated content injector, a composer, and a supervisor.

The summarizer is configured to generate a diagnostic narrative from a series of messages and replies. Thus, the summarizer forms a summary of the case or conversation between the computerized CBT therapy system and the patient. The summarizer also forms a patient profile, a comprehensive vector of relevant characteristics across various categories or dimensions of persona, demographics, goals, and limitations. Additionally, the summarizer detects and/or predicts missing information and generates anamnesis (guided recall) questions that can be fed to the composer. Overall, the summarizer provides a long-term memory representation of the system's interaction with the patient. As part of the long-term memory representation, the summarizer compresses the information from the messages and replies into a compact vector that can be fed to the composer. The compressed information enables maintenance of continuity in the conversation by keeping track of the patient's history, attributes, progress. The summarizer's representation of the interaction also enables provision of insight into the interaction. The summarizer operates in parallel to the other agents, so that its algorithm does not drive latency in the conversation.

The inner voice is configured to represent the cognitive process of an expert interlocutor. As such, the inner voice combines all available patient information (including the summarizer's representation of such information) with relevant professional knowledge to provide an expert assessment of the interaction and the patient's situation. Based on the expert assessment, the inner voice proposes relevant questions and/or suggestions that could be posed to the patient. The inner voice thereby plans a further course of action in the conversation. The inner voice operates independently of the summarizer, composer, and supervisor, working in parallel rather than sequentially. Once the inner voice formulates a new assessment, the assessment is stored in a history of the interaction for access and use by the composer. The inner voice, by operating in parallel to the other agents to plan the course of the conversation, enhances response speed from the patient's perspective by preparing assessments ahead of time. Unlike a human conversation, the system is fully capable of both receiving a message and planning a response in parallel. Thus, the inner voice enables enhanced or superior active listening.

The curated content injector ("CCI") is an agent that responds to the expert assessment produced by the inner voice. The CCI provides pre-curated content elements such as: relaxation audios; in-depth motivational or information-seeking questions; conversational interventions; educational content; and/or instructions for responding to crises (e.g., in a psychotherapeutic context, suicidal ideation, adverse side effects of a given drug, ineffective drug dosage levels, etc.). The curated content can include, e.g., audio, image, and text elements in any combination; videos and interactive elements. The CCI is intended to ensure that the patient receives pre-authored, well-targeted content exactly as intended by the authors. The CCI matches content to the patient's situation based on a numerical matching (e.g., cosine distance) between a vector embedding of the inner voice's expert assessment and vector embeddings of an assessment by an LLM when to use this content—not the content itself. Thus, the CCI provides a dynamic, automatic selection of conversational interventions and content, unprecedented in its capabilities. For example, the CCI may select the top five content elements that best fit (cosine distance match) the embedding of the current assessment of the patient's situation. The CCI then may provide these selected contents to the composer for potential inclusion in the response. In some embodiments, the composer may be obliged to include the curated content. In other embodiments, it may be optional for the composer to include the curated content.

The composer formulates drafts for a reply to the patient's message, based on all available information about the patient including the message itself, the inner voice's assessment and the summarizer's representation of the interaction with the patient. Thus, the composer utilizes information partially prepared by other agents. The composer tailors each reply to the specific needs and context of the patient. The composer maintains consistency in the conversation by harmonizing data from the other agents.

The composer does not send replies directly to the patient; instead, the supervisor reviews every reply and occasionally provides feedback to the composer. The supervisor generates feedback based on a set of relevant professional knowledge, which may be the same professional knowledge that is used by the inner voice. Checking replies against professional knowledge can help to make replies appropriate within the context of the conversation. Thus, the supervisor can protect the computerized CBT therapy system against prompt injections and various malicious user requests. The supervisor is responsible for system boundary maintenance by ensuring that the overall system remains within the defined scope of the system's assigned purpose. The supervisor enhances the quality and safety of the system's replies, maintains consistent standards of expertise, and safeguards against potential misuse or harmful responses.

In response to feedback from the supervisor, the composer may produce revised draft replies.

DETAILED DESCRIPTION

Figure 1:
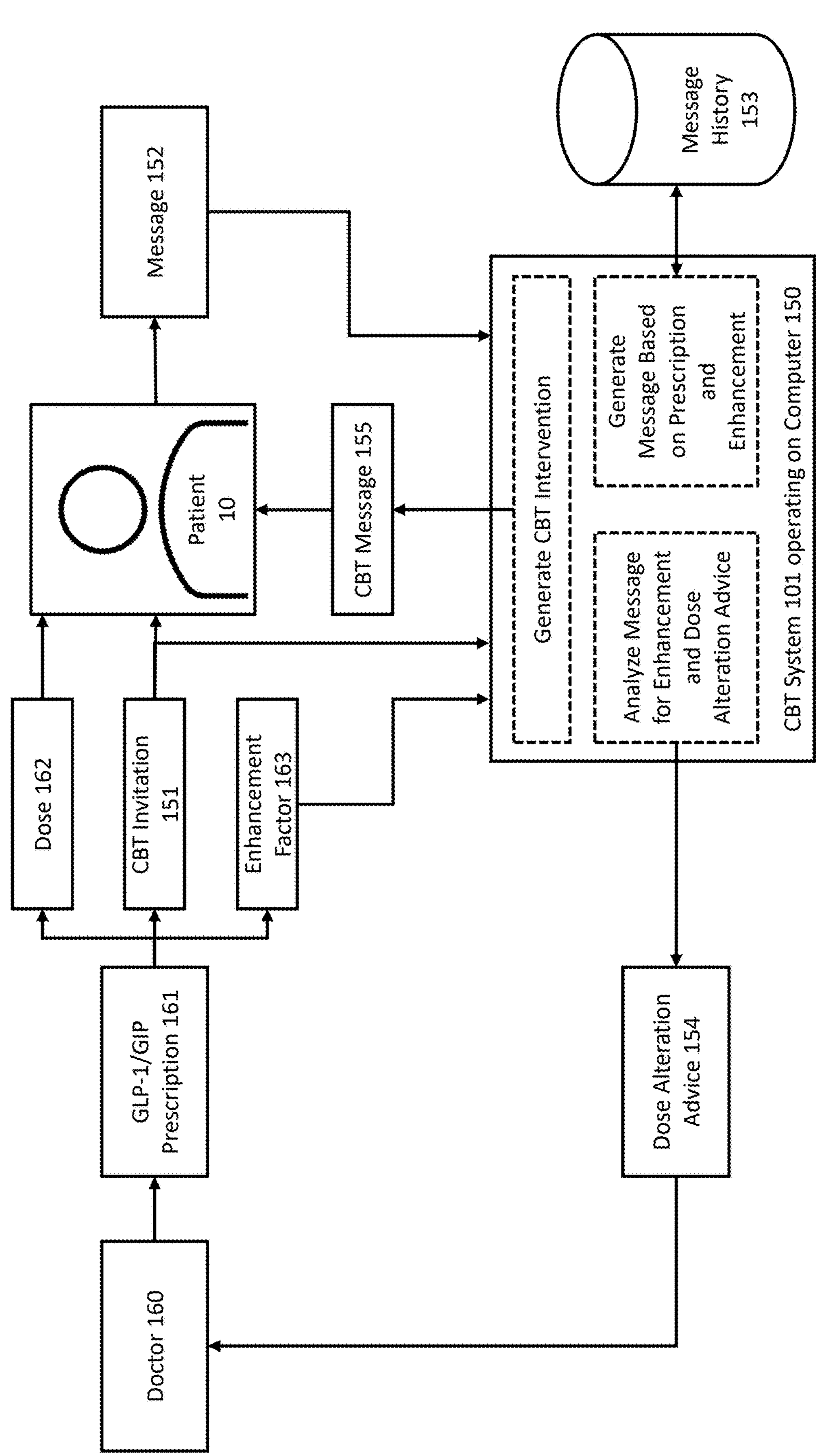
FIG. 1 is a depiction of a computerized cognitive behavioral therapy system influencing the effects of GLP-1 and GIP drugs taken by a patient.

For purposes of explanation and not limitation, specific details are set forth such as particular structures, architectures, interfaces, techniques, etc. in order to provide a thorough understanding. In other instances, detailed descriptions of well-known devices and/or methods are omitted so as not to obscure the description with unnecessary detail.

CBT and other psychotherapeutic interventions can have profound effects on the patient's brain, and particularly on the limbic system (which is crucial for emotional regulation). CBT and other psychotherapeutic interventions can impact a patient in the following ways:

Emotion Regulation: The limbic system includes structures or components, such as the amygdala, hippocampus, and parts of the thalamus and hypothalamus, which are central to managing emotions. Psychotherapy can modify the responses of these limbic system structures to stress and emotional stimuli.

For example, psychotherapy may reduce the hypersensitivity of the amygdala to perceived (external) threats, thereby reducing feelings or manifestations of anxiety and depression in the patient.

Stress Response: Psychotherapy may alter how the limbic system reacts to stress. By changing thought patterns and emotional responses of a patient to stress, psychotherapy may reduce the activation of the hypothalamic-pituitary-adrenal ("HPA") axis, which is often overactive in patients with chronic stress For example, psychotherapy may reduce excessive activations of the HPA axis, thereby decreasing cortisol levels in the patient and accordingly reducing the overall stress burden on the body.

Neuroplasticity: Through the process of neuroplasticity, psychotherapy may encourage the formation of new neural connections within the limbic system. These new neural connections change the manner in which the patient processes and expresses emotions in response to external stimuli.

For example, psychotherapy may increase connectivity between the prefrontal cortex and the limbic system, thereby enhancing the patient's ability to apply rational thought to control or modulate emotional reactions, resulting in an improvement in the patient's overall emotional stability.

Memory Processing: Psychotherapy may modify the manner in which a patient forms and processes memories. The hippocampus, a component of the limbic system, plays a significant role in forming new memories and processing emotional context. Techniques introduced to a patient through psychotherapy may allow a patient to better control reactions and expressions of already-present memories and re-shape those memories through integrating the emotional and factual aspects of the memories more effectively, thereby reducing the emotional intensity of those memories.

For example, psychotherapy may allow a patient to implement trauma-focused memory processing, thereby reshaping traumatic memories the patient has and allowing the patient to respond to those memories in a less intense manner.

Behavioral Changes: Psychotherapy may introduce changes in the limbic system which manifest in the patient's behavior (e.g., changes in behavior of the patient in response to inputs which are interpreted or processed through components of the limbic system). Changes to the emotional landscape of a patient's brain through psychotherapy may result in the patient finding it easier to engage in behaviors which were previously difficult to engage in.

For example, psychotherapy may allow a patient to remain calm in situations which (prior to treatment) would traditionally have caused panic in the patient. As another example, patients may also be able to alter habitual responses (e.g., drinking alcohol) to emotional triggers (e.g., stress).

FIG. 1 depicts an overall interaction of a computerized CBT therapy system 101 operating on a computer 150 and interacting with a patient 10. Patient 10 may have a pre-existing relationship with doctor 160 who has prescribed a GLP-1 or GIP drug 161 ("prescription") to patient 10.

The prescription 161 may include a dose 162 and an enhancement factor 163. An initial dose may be prescribed by the doctor 160 based on generic aspects of the patient 10, such as their height, weight, age, underlying medical conditions, and so on. Alternatively, or in conjunction with this embodiment, no doctor may be present where the prescription 161 may be obtained directly by the patient 10 without the assistance of a medical professional.

The enhancement factor 163 may be one or more of: a reduction in the anxiety and depression experienced by the patient; a reduction in cortisol levels or stress burden experienced by the patient; an increase in the neuroplasticity and overall emotional stability of the patient; an improvement in the memory processing and reduction of emotional intensity of memories of the patient; or behavioral changes and reduction of fear and habitual responses to stimuli experienced by the patient.

Patient 10 may receive a CBT invitation 151 with the goal of optimizing or improving the patient's response to the dose 162 or another aspect of the patient (e.g., one of the subjects of the enhancement factor 163). Patient 10 may interact with the computerized CBT therapy system 101 via message 152, copies of which are stored in the message history 153. For example, the computerized CBT therapy system 101 may request patient 10 describe their feelings about the prescription 161 or dose 162 and how the patient 10 has reacted to the medication. Alternatively, the computerized CBT therapy system 101 may communicate directly with the doctor 160 and not with the patient 10, and in such an embodiment the patient 10 is inputting information into the computerized CBT therapy system 101 via message 152 in a manner similar to that of a personal diary.

The computerized CBT therapy system 101 may analyze messages 152 which the patient 10 has transmitted and develop enhancement advice and/or dose alteration advice 154 which is then transmitted to the doctor 160. The computerized CBT therapy system 101 may further generate a CBT message 155 based on the prescription 161 and enhancement 163, and then transmit that CBT message directly to the patient 10.

Figure 2:
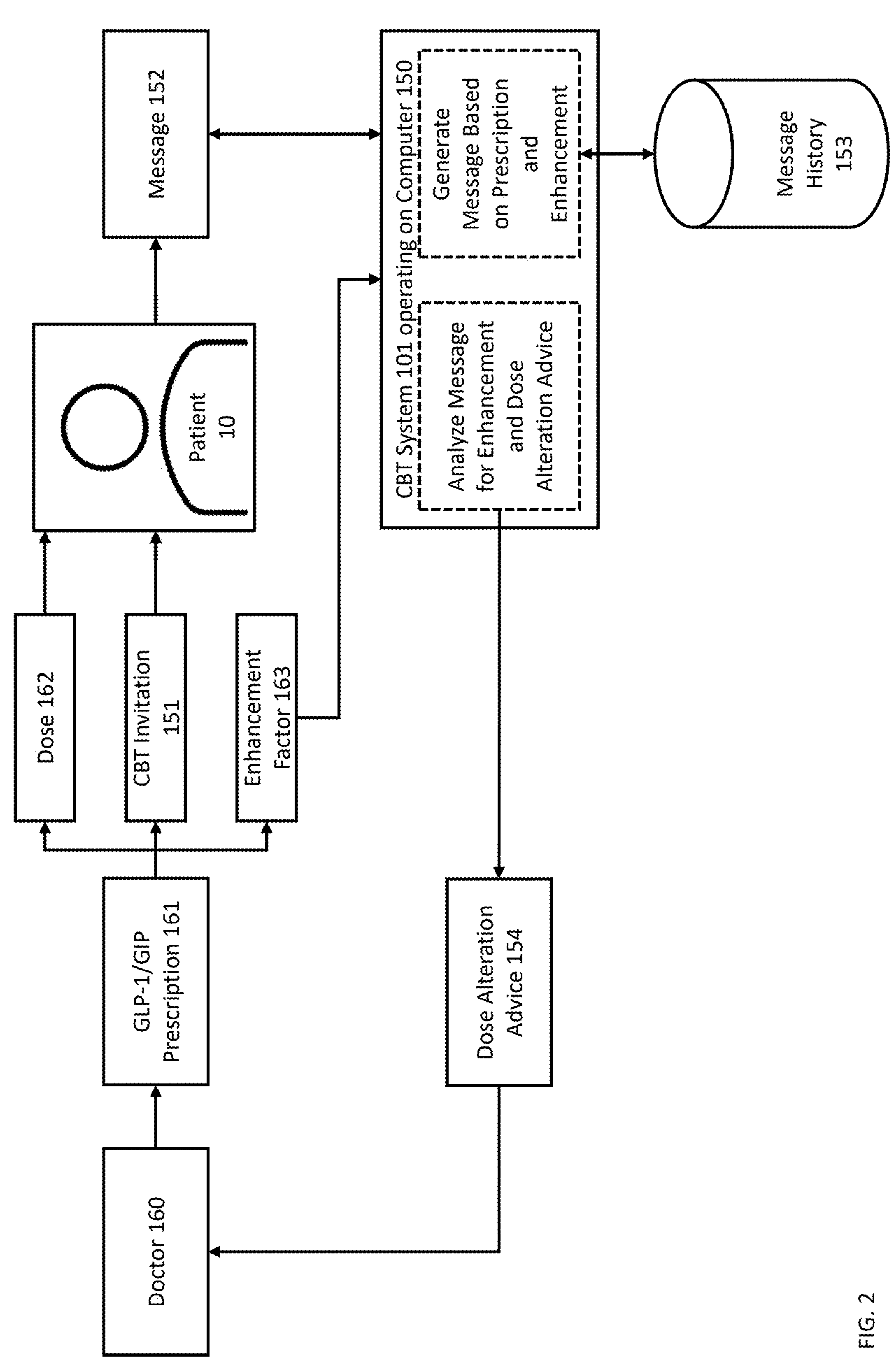
FIG. 2 is a depiction of a computerized system influencing the dosage of GLP-1 and GIP drugs taken by a patient.

FIG. 2 depicts an overall interaction of a computerized CBT therapy system 101 with a patient 10 where no CBT is provided to the patient 10 by the computerized CBT therapy system 101.

Figure 3:
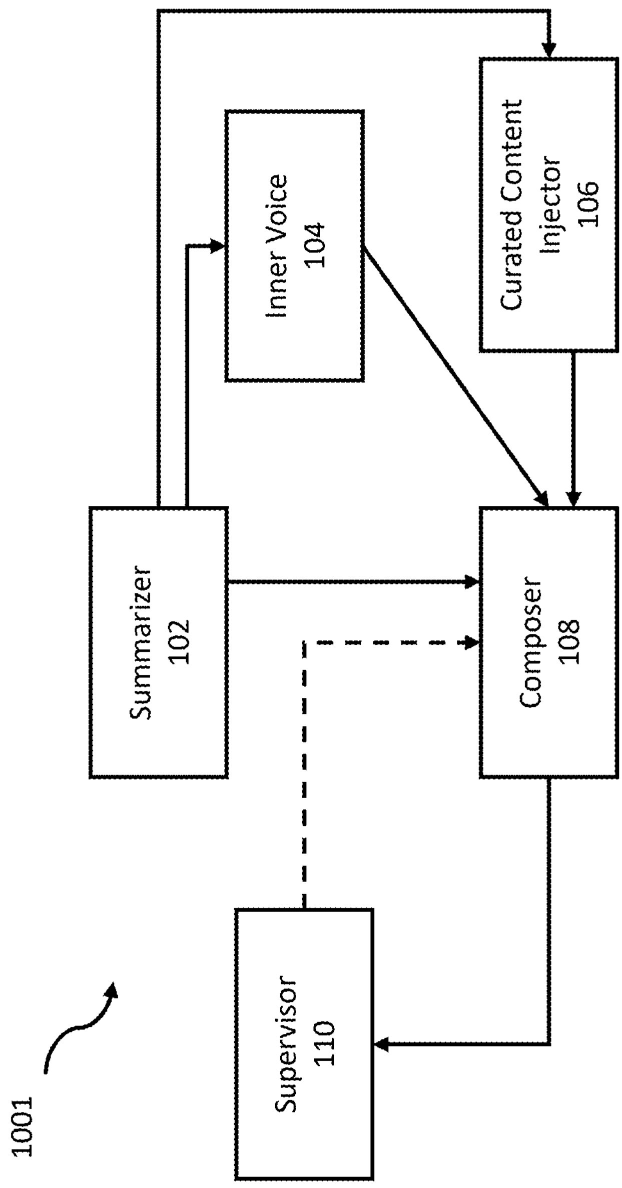
FIG. 3 depicts a high-level interaction 1001 of one embodiment of a computerized CBT therapy system 101 comprised of a supervisor 110, summarizer 102, inner voice 104, composer 108, and curated content injector 106.

FIG. 3 depicts a high-level interaction 1001 of one embodiment of a computerized CBT therapy system 101 comprised of a supervisor 110, summarizer 102, inner voice 104, composer 108, and curated content injector 106. In the depicted embodiment, lines of communication are shown. For example, the supervisor 110 may receive information, such as a draft reply 134, from the composer 108. In some instances, the supervisor may transmit supervisor feedback 138 to the composer 108. As shown, the summarizer 102, inner voice 104, curated content injector 106, and supervisor 110 may all be in communication with the composer 108 in a computerized CBT therapy system 101 according to the present teachings.

Figure 4:
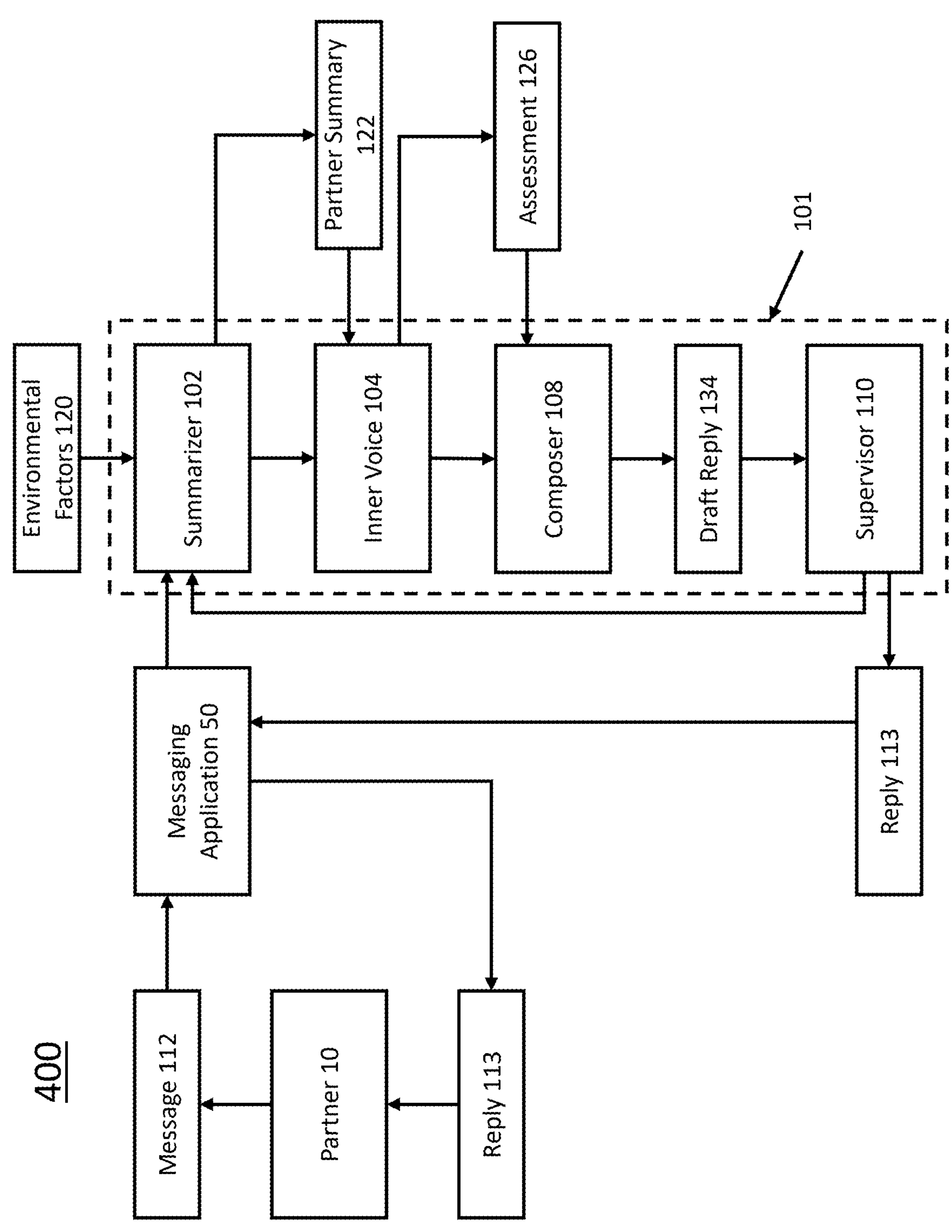
FIG. 4 depicts an overall interaction 400 of a computerized CBT therapy system 101 with a partner 10, consistent with selected aspects of the disclosure.

FIG. 4 depicts an overall interaction 400 of a computerized CBT therapy system 101 with a patient 10, consistent with selected aspects of the disclosure. The computerized CBT therapy system 101 repeatedly receives a message 112 from the patient 10 (e.g., a therapy patient), via a messaging app 50, and delivers a reply 113 to the patient 10. A supervisor 110 may intermediate the reply 113 and provide feedback to the computerized CBT therapy system 101. The computerized CBT therapy system 101 produces the reply 113 based on one or more of the message 112, a patient (patient) summary 122, environmental factors 120, and/or an expert (therapeutic) assessment 126.

Figure 5:
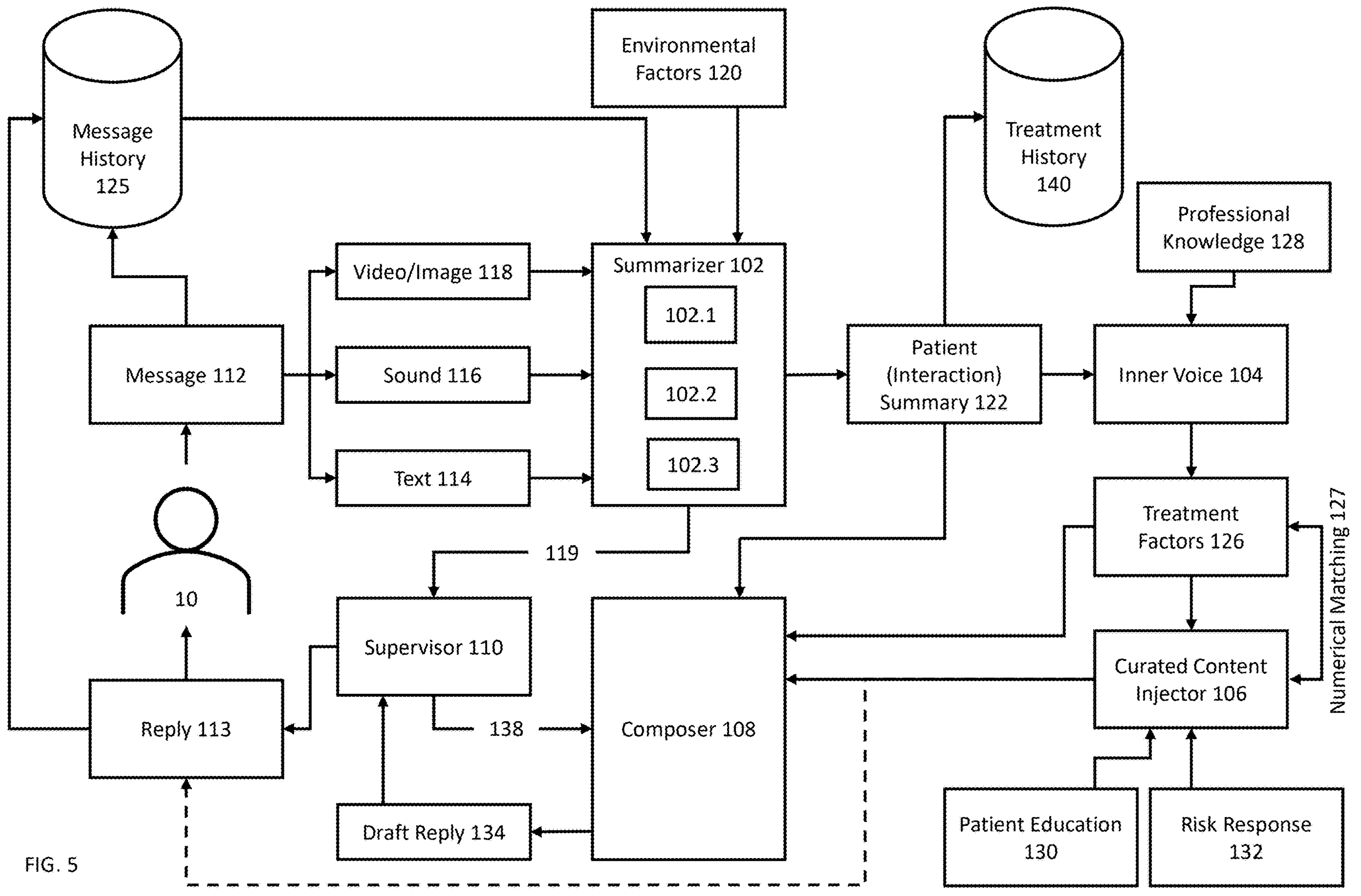
FIG. 5 depicts an embodiment of the computerized CBT therapy system 101 shown in FIG. 4

FIG. 5 depicts details of the computerized CBT therapy system 101. The computerized CBT therapy system 101 includes a summarizer 102, an inner voice 104, a curated content injector 106, a composer 108, and a supervisor 110.

In operation of the computerized CBT therapy system 101, the summarizer 102 receives the message 112 from the patient 10. The message 112 includes one or more of text 114, sound 116, and/or video/image data 118. The summarizer encodes the audio and/or video data as alt text and compiles the alt text with the message text 114 to form a full text 119. The summarizer sends the complete text 119 to the supervisor 110. The summarizer includes another encoder neural network 102.1 that is configured to compile the message 112 (optionally, in combination with sensed environmental factors 120) with one or more previous messages to produce an interaction (therapy) summary 122, which is a long-term memory representation of the interaction or conversation that the computerized CBT therapy system 101 has with the patient 10. The summarizer also includes a generative neural network 102.2 that is configured to produce a patient (patient) profile 123 based on the interaction summary 122 using weights that are encoded with professional (therapeutic) knowledge 128. The summarizer 102 also may include a generative neural network 102.3 that is configured to identify gaps or missing information in the patient summary 122 and may be further configured to generate information-seeking or anamnesis questions 124 based on the patient summary 122. The summarizer 102 may be implemented, for example, as an encoder network. The summarizer 102 also may be implemented as a portion of a long, short-term memory (LSTM) neural network. The summarizer 102 stores the patient summary 122 in a message history database 125 and also feeds the patient summary 122 to the inner voice 104.

The inner voice 104 is configured to generate an assessment of treatment factors 126 including the patient and the interaction with the patient, based at least on the patient summary 122 and a set of professional (therapeutic) knowledge 128. The inner voice 104 may be configured, for example, as an encoder or as a transformer network that takes at least the patient summary 122 as a prompt. The set of professional knowledge 128 may be input to the inner voice 104 as a complex (many token, e.g., thousands of tokens) prompt, and/or may be encoded in the weights of the inner voice 104 in case the inner voice 104 is implemented as a large language model (LLM) or other type of neural network. The assessment 126 may be in the form of a multi-dimensional vector that diagnoses or describes the patient and the interaction across dimensions such as persona, demographics, goals, and limitations. The inner voice 104 feeds the assessment 126 to the composer 108, and also feeds the assessment 126 to the curated content injector 106.

The curated content injector 106 may match the assessment 126 to one or more items of curated content such as patient education 130 and/or risk response information 132, in order to identify any curated content that should be imparted to the composer 108. For example, the curated content injector 106 may vectorize the assessment 126 in a semantic space and then perform vector matching (e.g., cosine distance) between the vectorized assessment and respective semantic space vectors of the curated content.

The composer 108 is configured to receive at least the message 112, the patient summary 122, and the assessment 126, as well as (optionally) curated content 130, 132. The composer 108 may be implemented as a generative adversarial neural network ("GAN") (e.g., using transformer architecture) that takes a compilation of the message 112, the patient summary 122, and the assessment 126 as a prompt, and may take the curated content 130, 132 either as an overriding prompt or as an addition to the prompt including the other content. The composer weights may be trained on a set of situational data, questions, and suggestions. The composer 108 is configured to deliver one or more draft replies 134 to the supervisor 110.

The supervisor 110 is configured to receive the draft replies 134 from the composer 108. The supervisor 110 may be implemented as a GAN that takes only the set of professional knowledge 128 and the current message 112 as inputs, produces a set of model replies, and uses a vector distance algorithm that compares each draft reply to each of the set of model replies. In case the supervisor 110 finds no close match, then the supervisor 110 may provide feedback 138 to the composer 108, thus prompting a revised set of draft replies.

At each iteration of message 112 and reply 113, the computerized CBT therapy system 101 stores these communications in the message history 125. The computerized CBT therapy system 101 also stores a compilation of patient summaries 122 in a treatment history 140.

A prototype of the computerized CBT therapy system operates on multiple instances of GPT-4 by OpenAI. Open-source models such as LLaMA 3 are equally suitable. The computerized CBT therapy system may be self-hosted. Using multiple instances of large language models (LLMs) that take separate customized prompts and/or are trained on custom data enables the computerized CBT therapy system 101 to produce high-quality responses. LLMs can provide powerful capabilities for processing and generating human-like text. Moving to open-source models may enhance scalability and provide greater control over the system. For example, using a self-hosted open-source model may allow for customization and fine-tuning to meet specific support needs. Additionally, self-hosting ensures higher security and better privacy for user data. As an alternative or supplement to fine-tuning with data, embodiments of the computerized CBT therapy system may utilize advanced prompt engineering (for example, based on a database of curated prompts) for effective responses.

In various applications, certain components of the computerized CBT therapy system 101 may serve distinct roles. For example, if the computerized CBT therapy system 101 is implemented in a psychotherapeutic role, then the patient summary 122 may be better described as a patient summary 122, while the assessment 126 may be better described as treatment factors 126. In such an application, the curated content may be better described as patient education 130 and risk response 132.

Figure 6:
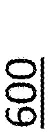
FIG. 6 depicts inputs to a prompt 600 for an inner voice 104 of the computerized CBT therapy system 101.
Figure 6:
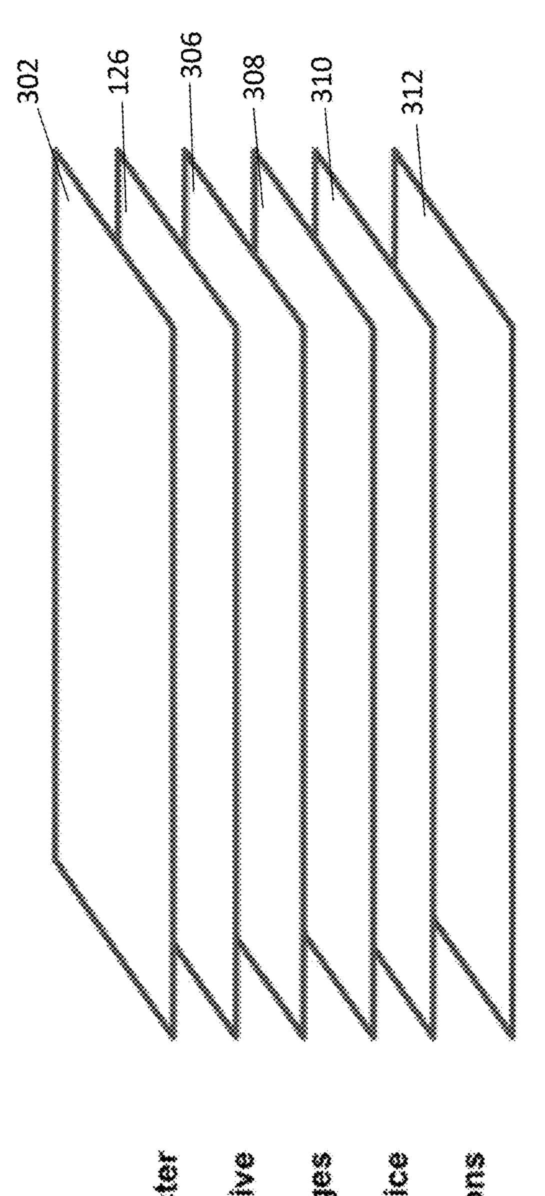

FIG. 6 depicts inputs to a prompt 600 for an inner voice 104 of the computerized CBT therapy system 101. The prompt 600 incorporates a therapeutic character 302, the therapeutic clinical narrative or assessment 126, a compilation of the last messages 306 (e.g., the six most recent messages), an echo of the last inner voice output 308, constraints and instructions 310, and a current time 312.

Options for the therapeutic character 302 include age, gender, race, education, and other aspects of a notional therapist's identity that are compiled into a framing portion of the prompt 600.

The therapeutic assessment 126 is an expert encoding or assessment of the message history as discussed above.

One purpose of the echo 308 is to maintain a continuity of context across multiple message and reply sequences.

The constraints and instructions 310 may include, for example, a constraint to acknowledge but not affirm negative messaging; a constraint to redirect attacks on the therapist/chat bot (where applicable); a constraint to ignore attacks on the therapist/chat bot (where applicable); an instruction to focus or perseverate on a given issue of concern to the patient/patient; an instruction to elicit additional detail from vague statements; etc.

Figure 7:
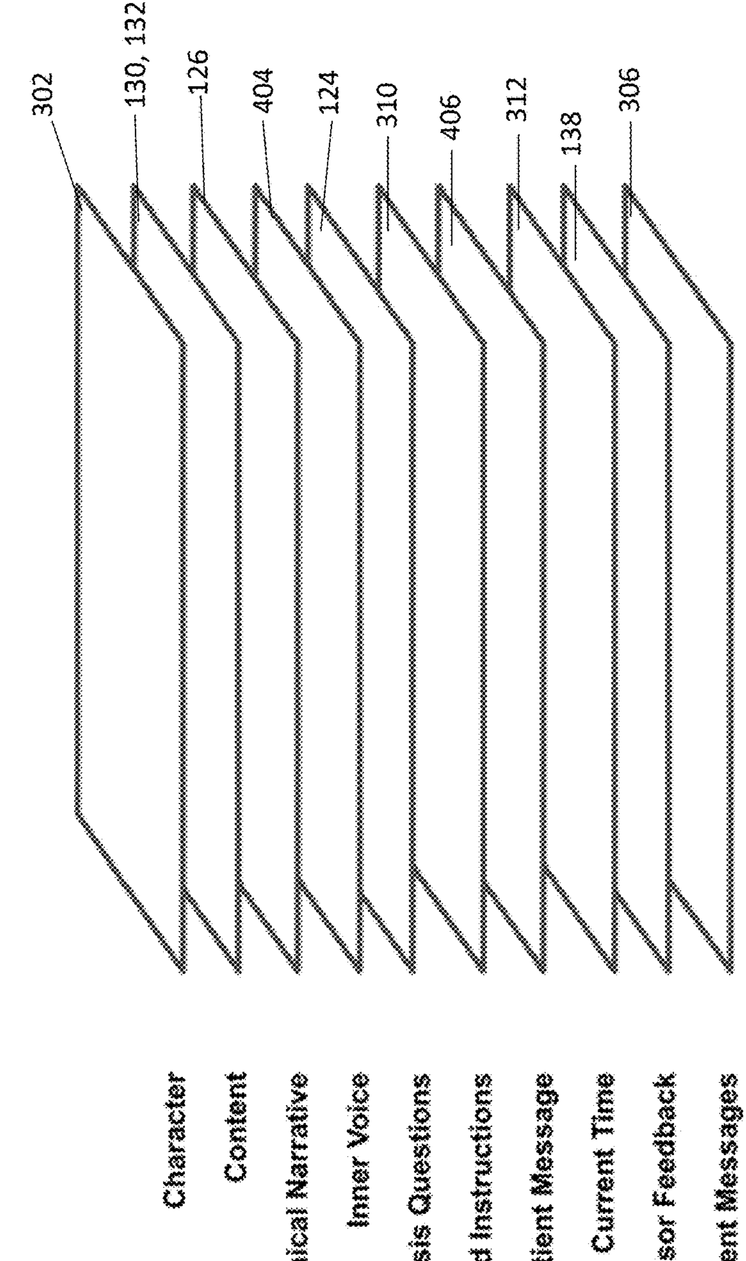
FIG. 7 depicts inputs to a prompt 700 for a composer 108 of the computerized CBT therapy system 101.

FIG. 7 depicts inputs to a prompt 700 for a composer 108 of the computerized CBT therapy system 101. The prompt 700 includes the therapeutic character 302, curated content 130, 132, therapeutic clinical narrative or assessment 126, inner voice output 404, missing information and anamnesis questions 124, constraints and instructions 310, time since last patient message 406, current time 312, supervisor feedback 138, and last patient messages 306.

As mentioned, the summarizer produces the anamnesis questions 124. The inner voice output 404 is produced by the inner voice 104 in response to the prompt 600.

Figure 8:
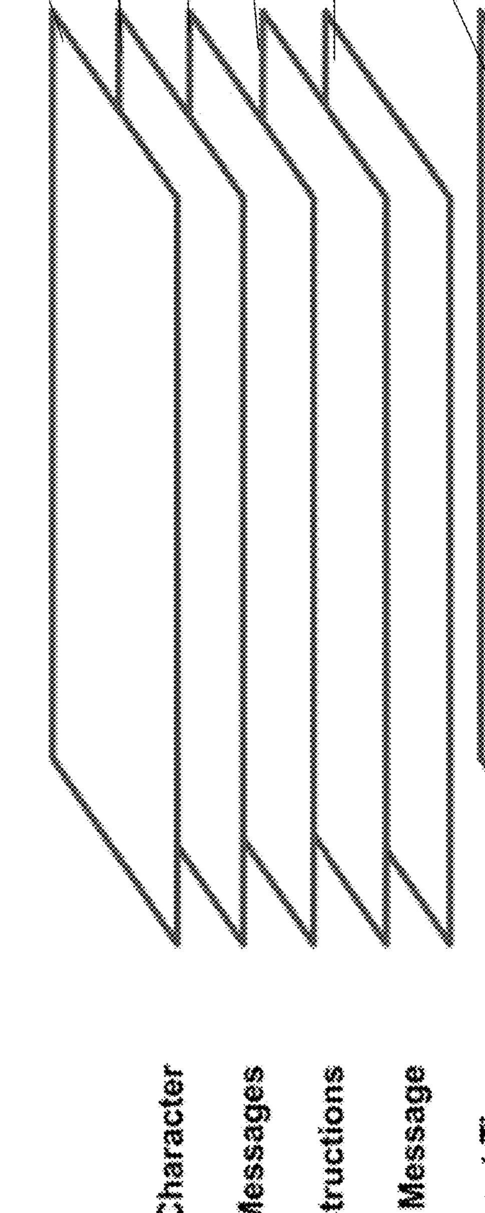
FIG. 8 depicts inputs to a prompt 800 for a supervisor 110 of the computerized CBT therapy system 101.

FIG. 8 depicts inputs to a prompt 800 for a supervisor 110 of the computerized CBT therapy system 101. The prompt 800 includes supervisor character 502, last messages 306, constraints and instructions 310, time since last patient message 406, current time 312, and draft reply or replies 134.

The supervisor character 502 is distinct from the therapeutic character 302 in at least one dimension of age, gender, race, education, or other identity factors. Advantageously, this gives the effect of multiple perspectives on the task at hand.

The present teachings have been described in language more or less specific as to structural, mechanical, and functional features. It is to be understood, however, that the present teachings are not limited to the specific features shown and described, since the apparatus, system, and/or method herein disclosed comprises preferred forms of putting the present teachings into effect.

Generally, all terms used in the claims are to be interpreted according to their ordinary meaning in the technical field, unless explicitly defined otherwise herein. All references to a/an/the element, apparatus, component, means, step, etc. are to be interpreted openly as referring to at least one instance of the element, apparatus, component, means, step, etc., unless explicitly stated otherwise. The use of "first", "second," etc. for different features/components of the present disclosure are only intended to distinguish the features/components from other similar features/components and not to impart any order or hierarchy to the features/components, unless explicitly stated otherwise. The phrase "at least one of," when used with a list of items, means that different combinations of one or more of the listed items may be used, and only one item in the list may be needed. For example, "at least one of: A, B, and C" includes any of the following combinations: A; B; C; A and B; A and C; B and C; and A and B and C.

Other than in the operating examples, or where otherwise indicated, all numbers expressing quantities of ingredients or reaction conditions used herein are to be understood as modified in all instances by the term "about".

While the present teachings have been described above in terms of specific embodiments, it is to be understood that they are not limited to those disclosed embodiments. Many modifications and other embodiments will come to mind to those skilled in the art to which this pertains, and which are intended to be and are covered by both this disclosure and the appended claims. For example, in some instances, one or more features disclosed in connection with one embodiment can be used alone or in combination with one or more features of one or more other embodiments. It is intended that the scope of the present teachings should be determined by proper interpretation and construction of any claims and their legal equivalents, as understood by those of skill in the art relying upon the disclosure in this specification and the attached drawings.

What is claimed is:

1. A system for enhancing GLP-1/GIP drug effects, comprising:

a computer;

a prescription for GLP-1/GIP drugs delivered to a patient in a dose, said dose subject to modification via an enhancement factor;

a user device receiving a plurality of patient messages from the patient and transmitting said plurality of patient messages to the computer, each of said plurality of patient messages having a text portion and an emotional portion;

wherein the emotional portion includes a plurality of videos of the patient's face;

a database in communication with the computer, said database pre-loaded with a plurality of curated content and a plurality of defined safety parameters and further configured to accept additional contributions;

software executing on the computer comprising a summarizer agent, said summarizer agent configured to receive the patient messages and generate a patient textual sentiment vector and a patient facial emotion vector and a long-term memory vector representation of the patient and the patient messages, said summarizer agent further configured to store the plurality of patient messages and the patient textual sentiment vector and the patient facial emotion vector and the long-term memory vector representation of the patient and the patient messages in the database;

software executing on the computer comprising a inner voice agent, said inner voice agent configured to operate in parallel with the summarizer agent, said inner voice agent further configured to generate a strategic therapeutic assessment vector and an enhancement factor vector based on professional knowledge constraints;

software executing on the computer comprising a curated content injector, said curated content injector configured to perform numerical vector matching between the strategic therapeutic assessment vector and the enhancement factor vector and one or more of the plurality of curated content and configured to select one or more of the plurality of curated content;

software executing on the computer comprising a composer agent, said composer agent configured to generate a draft reply to the patient message and a draft enhancement factor modification, said draft reply and said draft enhancement factor modification generated by the composer agent by synthesizing the patient message and the strategic therapeutic assessment vector and the enhancement factor vector and one or more of the plurality of curated content selected by the curated content injector;

software executing on the computer comprising a supervisor agent, said supervisor agent configured to:

analyze the draft reply and the draft enhancement factor modification against one or more defined safety parameters in the database;

identify incongruity between the text portion and the emotional portion of the patient messages by calculating the divergence between the patient textual sentiment vector and the patient facial emotion vector;

authorize the composer agent to generate a final reply and a final enhancement factor modification if the defined safety parameters are met; and transmit the final reply and the final enhancement factor modification from the computer to the mobile computing device via the telecom network.

2. The system of claim 1, wherein the final reply and the final enhancement factor modification provided by the computer to the patient is an emotional regulation message and the desired enhancement is a reduction in the anxiety and depression experienced by the patient.

3. The system of claim 1, wherein the final reply and the final enhancement factor modification provided by the computer to the patient is a stress response message and the desired enhancement is a reduction in cortisol levels or stress burden experienced by the patient.

4. The system of claim 1, wherein the final reply and the final enhancement factor modification provided by the computer to the patient is a stress response message and the desired enhancement is an increase in the neuroplasticity and overall emotional stability of the patient.

5. The system of claim 1, wherein the final reply and the final enhancement factor modification provided by the computer to the patient is a stress response message and the desired enhancement is an improvement in the memory processing and reduction of emotional intensity of memories of the patient.

6. The system of claim 1, wherein the final reply and the final enhancement factor modification provided by the computer to the patient is a stress response message and the desired enhancement is behavioral changes and reduction of fear and habitual responses to stimuli experienced by the patient.

7. A system for enhancing GLP-1/GIP drug effects, comprising:

a prescription for GLP-1/GIP drugs delivered to a patient, said prescription having a dose and said dose subject to modification by an enhancement factor;

a mobile computing device;

a messaging app running on the mobile computing device;

a computer with access to the messaging app;

a database accessible by the computer, said database configured to accept additional contributions;

a communication channel established between the mobile computing device and the computer;

a plurality of messages received by the computer from the mobile computing device over the communication channel;

software executing on the computer for extracting at least one of audio, video and text data from each of the plurality of messages, and for producing a summary from the data, and storing a history of the messages and the summary of the data in the database;

software executing on the computer for generating from the at least one of audio, video, and text data from each of the plurality of messages at least one of a patient textual sentiment vector, a patient facial emotion vector, and an enhancement factor vector, and generating from the summary of the data a long-term memory vector representation of the patient and the patient messages;

the database further containing a plurality of curated replies processed to generate a numerical representation of each curated reply for storage together with the curated reply;

software executing on the computer with access to the database as well as environmental factors configured to perform numerical vector matching between at least one of the patient textual sentiment vector, the patient facial emotion vector, and the enhancement factor vector, and the long-term memory vector representation of the patient and the patient messages;

software executing on the computer for numerically representing the assessment and/or the message and for searching the curated reply database for matches;

software executing on the computer for generating a reply to the message using at least one of the message, the summary, the therapeutic assessment, the enhancement factor modification, and any matching curated content;

software executing on the computer for analyzing the reply and either returning it to the reply generating software for revision or forwarding it to the communication channel for transmission to the mobile computing device;

wherein, once the reply is forwarded to the communication channel it is added to the database of messages to form a conversation history; and software executing on said computer for analyzing response messages received from the patient to determine if the desired enhancement is being achieved, and, if appropriate, for recommending dese-alteration advice for the dose of said prescription.

8. A system for enhancing GLP-1/GIP drug effects, comprising:

a prescription for GLP-1/GIP drugs delivered to a patient;

a CBT invitation including an enhancement factor for said prescription;

a database pre-loaded with a plurality of curated content and a plurality of defined safety parameters and further configured to accept additional contributions;

a computer configured to be in communication with the database, said computer receiving said CBT invitation and the enhancement factor and establishing a communication link with the patient, said computer configured to receive a plurality of patient messages from the patient, each of said plurality of patient messages having a text portion and an emotional portion;

wherein said computer comprises a data capture module, an AI analysis module, a content delivery rules engine, and a display interface;

said AI analysis module comprising:

software executing within the AI analysis module comprising a summarizer agent, said summarizer agent configured to receive the patient messages and generate a patient textual sentiment vector and a patient facial emotion vector and a long-term memory vector representation of the patient and the patient messages, said summarizer agent further configured to store the plurality of patient messages and the patient textual sentiment vector and the patient facial emotion vector and the long-term memory vector representation of the patient and the patient messages in the database;

software executing within the AI analysis module comprising a inner voice agent, said inner voice agent configured to operate in parallel with the summarizer agent, said inner voice agent further configured to generate a strategic therapeutic assessment vector and an enhancement factor vector based on professional knowledge constraints;

software executing within the AI analysis module comprising a curated content injector, said curated content injector configured to perform numerical vector matching between the strategic therapeutic assessment vector and the enhancement factor vector and one or more of the plurality of curated content and configured to select one or more of the plurality of curated content;

said data capture module comprising one or more sensors capable of capturing one or more of text, voice, and images;

wherein the data capture module, AI analysis module, content delivery rules engine, and display interface are in electronic communication;

software executing on said computer for analyzing response messages received from the patient to determine if the desired enhancement is being achieved, and, if appropriate, for recommending dose alteration advice for said prescription, said software comprising a composer agent, said composer agent configured to generate a draft reply to the patient message and a draft enhancement factor modification, said draft reply and said draft enhancement factor modification generated by the composer agent by synthesizing the patient message and the strategic therapeutic assessment vector and the enhancement factor vector and one or more of the plurality of curated content selected by the curated content injector;

software executing within the content delivery rules engine comprising a supervisor agent, said supervisor agent configured to:

analyze the draft reply and the draft enhancement factor modification against one or more defined safety parameters in the database;

identify incongruity between the text portion and the emotional portion of the patient messages by calculating the divergence between the patient textual sentiment vector and the patient facial emotion vector;

authorize the composer agent to generate a final reply and a final enhancement factor modification if the defined safety parameters are met; and transmit the final reply and the final enhancement factor modification from the computer to the display interface.

9. The system of claim 8, wherein the content delivery rules engine employs a set of rules comprising one or more rules to determine which text, voice, and/or image content should be displayed on the display interface.

10. The system of claim 9, wherein the rules comprise one or more of selecting content, prioritizing types of content, adjusting frequency and timing of messages, intensifying intervention, and incorporating real-time data based on previous communication with the patient.

11. The system of claim 8, comprising a user reaction capture device, wherein said user reaction capture device includes one or more sensors capable of capturing user reactions in the form of text, audio, and/or facial images.

* * * * *